US009545470B2

(12) United States Patent
Lee et al.

(10) Patent No.: US 9,545,470 B2
(45) Date of Patent: Jan. 17, 2017

(54) DIALYSIS CONNECTOR AND CAP COMPATIBLE WITH GAS STERILIZATION

(71) Applicants: Baxter International Inc., Deerfield, IL (US); Baxter Healthcare S.A., Glattpark (Opfikon) (CH)

(72) Inventors: Patrick Jong Lee, Long Grove, IL (US); Serhan Acikgoz, Des Plaines, IL (US); Yuanpang Samuel Ding, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 443 days.

(21) Appl. No.: 14/098,197

(22) Filed: Dec. 5, 2013

(65) Prior Publication Data

US 2014/0094740 A1 Apr. 3, 2014

Related U.S. Application Data

(63) Continuation of application No. 12/560,022, filed on Sep. 15, 2009, now Pat. No. 8,617,465.

(51) Int. Cl.
| | | |
|---|---|---|
| *A61M 1/28* | (2006.01) | |
| *A61L 2/20* | (2006.01) | |
| *A61M 1/16* | (2006.01) | |
| *A61L 2/08* | (2006.01) | |

(52) U.S. Cl.
CPC ............... *A61M 1/28* (2013.01); *A61L 2/206* (2013.01); *A61M 1/169* (2013.01); *A61L 2/081* (2013.01); *A61M 2205/12* (2013.01)

(58) Field of Classification Search
CPC ........ A61M 1/28; A61M 1/169; A61M 39/20; A61L 2/20–2/208
See application file for complete search history.

(56) References Cited

U.S. PATENT DOCUMENTS

| | | |
|---|---|---|
| 3,631,382 A | 12/1971 | Paine et al. |
| 3,650,093 A | 3/1972 | Rosenberg |
| 3,986,508 A | 10/1976 | Barrington |
| 4,209,013 A | 6/1980 | Alexander et al. |
| 4,334,551 A | 6/1982 | Pfister |
| 4,412,834 A | 11/1983 | Kulin et al. |
| 4,417,890 A | 11/1983 | Dennehey et al. |
| 4,457,749 A | 7/1984 | Bellotti et al. |
| 4,469,835 A | 9/1984 | Laurin |
| 4,503,333 A | 3/1985 | Kulin et al. |
| 4,588,402 A | 5/1986 | Igari et al. |
| 4,668,217 A | 5/1987 | Isono |
| 4,691,557 A | 9/1987 | Dunn et al. |
| 4,778,447 A | 10/1988 | Velde et al. |

(Continued)

*Primary Examiner* — Timothy Cleveland
(74) *Attorney, Agent, or Firm* — K&L Gates LLP (57) ABSTRACT

A dialysis disposable sterilization apparatus includes a connector and a protective cap fitted to the connector. The apparatus also includes a sealing ring provided by one of the protective cap or the connector, the sealing ring forming a seal between the cap and the connector, the seal capable of holding pressure. The apparatus further includes a stabilization rib provided by the connector, the stabilization rib positioned and arranged to (i) tend to prevent the protective cap from vibrating about the sealing ring and (ii) enable a sterilizing gas to flow past the stabilization rib to contact the sealing ring.

21 Claims, 5 Drawing Sheets

(56) References Cited

U.S. PATENT DOCUMENTS

| | | | |
|---|---|---|---|
| 4,816,221 A | 3/1989 | Harvey et al. | |
| 4,820,288 A | 4/1989 | Isono | |
| 4,950,230 A | 8/1990 | Kendell | |
| 4,991,629 A * | 2/1991 | Ernesto | A61M 39/20 138/89 |
| 5,058,619 A | 10/1991 | Zheng | |
| 5,190,534 A | 3/1993 | Kendell | |
| 5,195,957 A | 3/1993 | Tollini | |
| 5,257,832 A | 11/1993 | Phan et al. | |
| 5,263,860 A | 11/1993 | Shen et al. | |
| 5,275,724 A | 1/1994 | Bucchianeri et al. | |
| 5,279,605 A | 1/1994 | Karrasch et al. | |
| 5,280,809 A | 1/1994 | Tive | |
| 5,290,253 A | 3/1994 | Kira | |
| 5,303,751 A | 4/1994 | Slater et al. | |
| 5,536,258 A | 7/1996 | Folden | |
| 5,707,086 A | 1/1998 | Treu et al. | |
| 5,782,808 A | 7/1998 | Folden | |
| 5,855,230 A | 1/1999 | Guala et al. | |
| 5,879,328 A | 3/1999 | Holmberg et al. | |
| 5,932,132 A | 8/1999 | Plemons | |
| 6,041,794 A | 3/2000 | Lin et al. | |
| 6,077,259 A | 6/2000 | Caizza et al. | |
| 6,117,084 A | 9/2000 | Green et al. | |
| 6,203,522 B1 | 3/2001 | Holmberg et al. | |
| 6,309,358 B1 | 10/2001 | Okubo | |
| 6,354,312 B1 | 3/2002 | Lin et al. | |
| 6,394,983 B1 | 5/2002 | Mayoral et al. | |
| 7,198,611 B2 | 4/2007 | Connell et al. | |
| 2003/0153865 A1 | 8/2003 | Connell et al. | |
| 2004/0062694 A1 | 4/2004 | Vandlik et al. | |
| 2005/0197646 A1 | 9/2005 | Connell et al. | |
| 2005/0251096 A1 | 11/2005 | Armstrong et al. | |
| 2007/0106205 A1 | 5/2007 | Connell et al. | |
| 2008/0065000 A1 | 3/2008 | Bidinger et al. | |
| 2008/0132876 A1 | 6/2008 | Felt | |
| 2008/0265561 A1 | 10/2008 | Buchanan et al. | |
| 2009/0124963 A1 * | 5/2009 | Hogard | A61M 1/16 604/30 |

* cited by examiner

DIALYSIS CONNECTOR AND CAP COMPATIBLE WITH GAS STERILIZATION

PRIORITY CLAIM

This application claims priority to and the benefit as a continuation application of U.S. patent application Ser. No. 12/560,022, now U.S. Pat. No. 8,617,465, filed Sep. 15, 2009, entitled, "DIALYSIS CONNECTOR AND CAP COMPATIBLE WITH GAS STERILIZATION", the entire contents of which are hereby incorporated by reference and relied upon.

BACKGROUND

The present disclosure relates to sterile medical fluid delivering and in particular to the delivering of a dialysis solution.

Due to disease or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

One type of dialysis is peritoneal dialysis. Peritoneal dialysis uses a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD") and automated peritoneal dialysis ("APD"). CAPD is a manual dialysis treatment, in which the patient connects an implanted catheter to a drain and allows a spent dialysate fluid to drain from the patient's peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about four hours. APD is similar to CAPD in that the dialysis treatment includes a drain, fill, and dwell cycle. APD machines, however, perform three to four cycles of peritoneal dialysis treatment automatically, typically overnight while the patient sleeps. Like CAPD, APD machines connect fluidly to an implanted catheter, to one or more sources or bags of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure. As with the manual process, several drain, fill, and dwell cycles will occur during APD. A "last fill" is typically used at the end of APD, which remains in the peritoneal cavity of the patient when the patient disconnects from the dialysis machine for the day.

Delivery of dialysis fluid to the patient needs to be as germ free as possible. Germs or pathogens reaching the patient's peritoneum can cause peritonitis. Peritonitis can cause the patient to feel extreme pain and if not treated properly can result in death. Different methods of sterilization are available, such as gamma radiation and ethylene oxide ("EtO") gas. Gamma radiation is advantageous because it works from the outside-in, such that the radiation can sterilize the interior surfaces of a structure that trap a volume of gas within the sterilized part, such as a cap.

Gamma radiation does however have some negative side effects. One side effect is that the sterilized part, e.g., clean medical grade plastic, tends to yellow. While such yellowing is not harmful to the patient, some patients may find the yellowed disposable part less aesthetically pleasing than a pristine looking clear plastic disposable. Second, gamma radiation can cause the sterilized part to have an odor, especially when the disposable has larger plastic surfaces, which can also be displeasureable to the patient.

A need therefore exists for an apparatus and method for sterilizing a sealed part, such as a cap, using a sterilizing gas, such as EtO.

SUMMARY

The present disclosure sets forth an apparatus and method for sterilizing (or at least substantially sterilizing) a sealed component or one component sealed to another component, such that they form a sealed compartment capable of holding a positive or negative pressure. The present apparatus and method are illustrated as using a tip protector, or cap, which encloses a fluid connector, such as a peritoneal dialysis fluid connector. The connector is illustrated as being a spike connector but does not have to be a spike connector and instead could be a female connector that becomes spiked by an external spike connector. The connector could extend from a disposable cassette directly or alternatively from a line or tube attached to the disposable cassette. Further alternatively, the connector could extend from a tube or pigtail that is attached to a supply bag, heater bag or drain bag. As will be appreciated from the following summary and description, the present system and method are not limited to a cop/connector combination and instead may be applied to other closed volumes found in medical fluid disposables, such as dialysis disposables.

In one embodiment, the base of the tip protector or cap includes a sealing rib or ring that extends fully around the inside wall of the cap. This sealing rib press-fits against an outer annular wall of the connector or spike tip. The press-fit is sufficient to hold a specified pressure, e.g., eight psig. While the sealing ring provides the necessary seal, additional structure on the inside wall of the cap is needed to contact the connector or spike to prevent the cap from vibrating with respect to the spike during shipping or otherwise prior to its use. This additional structure is formed so as not to create a separate sealed volume with the sealing rib or ring. For example, the structure could be an additional rib or ring that is not extend fully around the inside wall of the cap. In one embodiment, the additional structure is a segmented, discontinuous or semi-continuous rib or ring that extends around the inside wall of the cap. The semi-continuous ring can for example have notches or grooves to provide openings through the opening, and the press by the semi-continuous ring to reach one side of the base, continuous sealing ring. The additional rib does not thereby create a separate, trapped sealed volume with the base ring when the cap is press-fitted onto the connector or spike.

Alternatively, the additional structure is a vertical or slanted rib extending along the inner wall of the cap or tip protector. For example, the rib can be a spiraling rib that allows the sterilizing gas to thread or corkscrew its way to the sealing rib.

In yet another alternative embodiment, the sealing ring and/or any of the additional vibration stabilizing structures can be provided on the outer walls of the connector or spike instead of being provided on the inner wall of the cap or tip protector.

The above apparatus enables a method of sterilization to take place in which the outside of the cap is exposed to sterilizing gas such as ethylene oxide ("EtO"), which contacts and sterilizes or at least substantially sterilizes the underside of the sealing ring or rib, namely, the rib extending all the way around the cap. Sterilizing gas is also flowed through the connector or spike, around the outside of the connector, through the openings in (or around) the additional stabilizing structures to reach the opposing side of the sealing ring for sterilization. It has been found that line contact between the cap or tip and the connector or spike, which the sterilizing gas may not reach, does not pose a risk to the patient.

It is accordingly an advantage of the present disclosure to provide an improved apparatus and method for gas, e.g., EtO sterilization.

It is another advantage of the present disclosure to provide an improved apparatus and method for sterilizing (at least substantially) inner walls of a cap sealed to a disposable cassette or set.

It is a further advantage of the present disclosure to provide an improved apparatus and method for sterilizing (at least substantially) a sealed surface.

Additional features and advantages are described herein, and will be apparent from the following Detailed Description and the figures.

DETAILED DESCRIPTION

Figure 1:
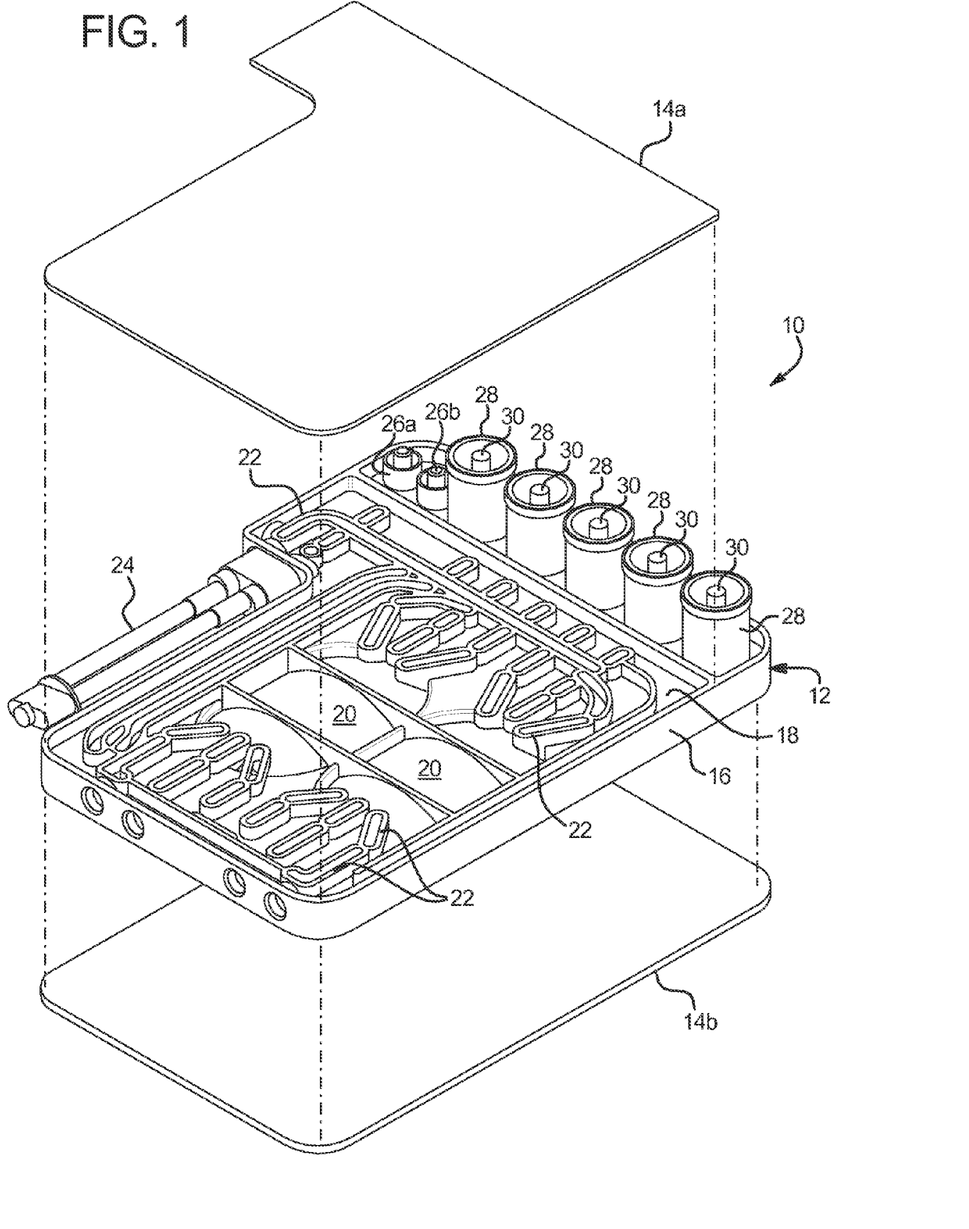
FIG. 1 is a perspective view of a disposable cassette having multiple port connectors that receive protective caps until the caps are removed so that a dialysate supply bag can be connected to the connector.
Figure 2:
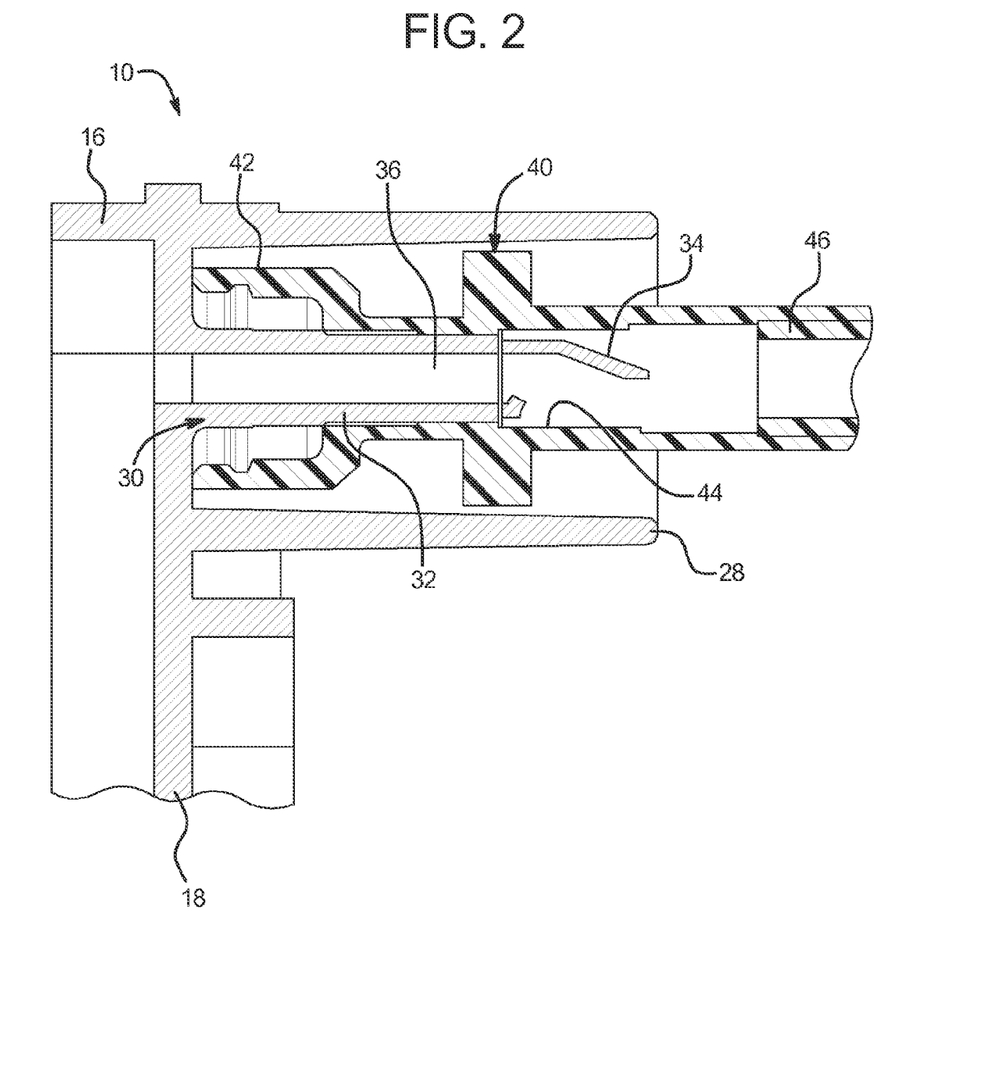
FIG. 2 is a side-sectional view of one of the connectors of the disposable cassette, wherein the connector is a spike connector that penetrates a female connector at the end of a supply bag tube.

Referring now to drawings and in particular FIGS. 1 and 2 disposable dialysis fluid pumping cassette 10 and corresponding supply connectors are illustrated. Pumping cassette 10 is operable in one embodiment with a peritoneal dialysis cycler as set forth in U.S. Pat. No. 7,955,295, filed Jul. 5, 2007, entitled "Fluid Delivery System With Autoconnect Features", the entire contents of which are incorporated herein by reference. Other relevant peritoneal dialysis machines are set forth in U.S. Pat. Nos. 5,350,357 and 7,410,175, the entire contents of each of which are incorporated herein by reference. While cassette 10 is described as being operable with a peritoneal dialysis machine, cassette 10 is alternatively operable with a different type of medical fluid machine, such as hemodialysis, hemofiltration or hemodiafiltration machine.

Still further alternatively, the connector and cap set forth herein does not extend from a cassette, such as cassette 10, but extends rather from an end of a tube, such as a supply bag tube or pigtail that extends from a supply bag 10 or container. The tube can alternatively can be attached to the cassette, such as cassette 10, wherein the connector and cap are placed at the distal non-cassette end of the tube.

Cassette 10 in the illustrated embodiment includes a rigid portion 12 and a pair of flexible sheets 14a and 14b welded to or otherwise sealed to rigid portion 12. Flexible sheets 14a and 14b are operated mechanically and/or pneumatically to open and close pumps and valves as disclosed in the above referenced patents. Rigid portion 12 includes a sidewall 16 and a base plate 18. Various structures arise from base plate 18, such as pumping chambers 20 and flow paths 22. Valve chambers, not illustrated because they reside on the other side of base plate 18, also extends out from the base plate 18.

In the illustrated embodiment, cassette 10 also includes an integrated inline heater 24. Cassette 10 includes a pair of ports 26a and 26b that are preattached to tubing that leads for example to a drain line or patient line. If batch heating is used instead of inline heating here via inline heater 24, the preattached tubing can run to a heater bag alternatively.

Cassette 10 further includes a plurality of shrouds 28 that extend outwardly from base plate 18. Although shrouds 28, and connectors 30 protected by the shrouds, are shown extended perpendicular to base plate 18, the connectors 30 and shrouds 28 can extend alternatively perpendicularly from sidewall 16. In another alternative embodiment, shrouds 28 are not provided and connectors 30 are instead exposed. In one embodiment, connectors 30 each connect to a supply line running from a dialysis fluid container or bag.

FIG. 2 illustrates connector 30 and shroud 28 in more detail. Connector 30 is illustrated having a base portion 32 that extends to a spike 34. Base section 32 and spike tip 34 define an interior lumen 36, which allows liquid from a supply bag to enter cassette 10. FIG. 2 illustrates that a supply bag connector 40 includes a female head 42, having a sheet or membrane that is pierced by spike 34 of connector 30. Connector 40 includes a body 44 that is sealed to an end of a supply tube 46. It should be appreciated that connector 30 does not have to be a spike connector and instead can be a female connector that is pierced by supply bag connector 40. In any case, once fluid communication is established between connectors 30 and 40, fresh dialysate or dialysis solution can flow from a supply bag or container (not illustrated) through supply tube 46, body portion 44 of female connector 40, lumen 36 of spike connector 30 and into cassette 10.

Figure 3:
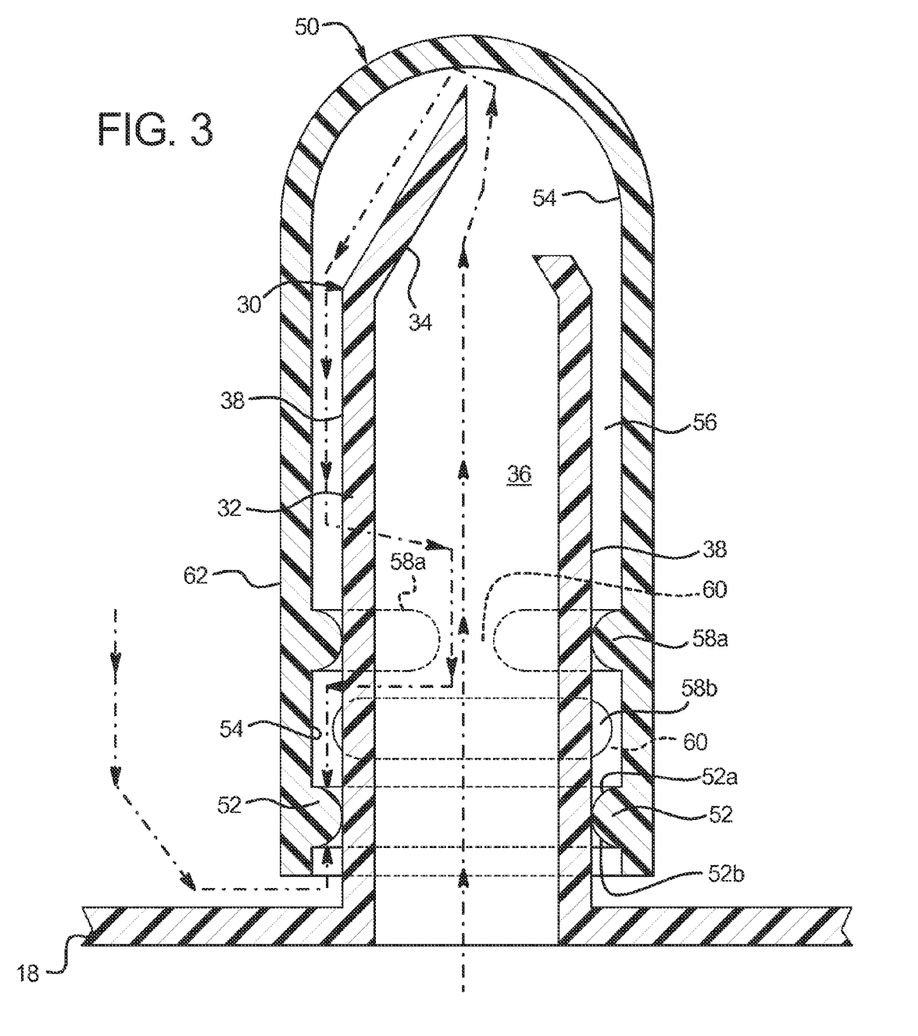
FIG. 3 is a side-sectional view illustrating one embodiment of a connector/cap construction of the present disclosure.

Referring now to FIG. 3, prior to spiking connector 40, a tip protector 50 is removed from spike connector 30. Tip protector 50 protects connector 30 and also seals the connector such that it can be sterilized. Again, connector 30 may be provided in different locations, such as the end of a supply tube. Even so, a tip protector, such as tip protector 50, is typically provided.

Tip protector 50 provides or includes a sealing ring 52 that extends continuously for 360 degrees around an inner wall of 54 of tip protector 50. Sealing ring 52 press-fits against an outer wall 38 of spike connector 30. The press-fit is configured to hold a desired amount of positive or negative pressure, such as plus or minus eight psig. That is, if the inner lumen 37 is pressurized with air or a sterilizing gas, such as ethylene oxide ("EtO"), lumen 56 between inner wall 54 of cap or tip protector 50 and outer wall 38 of spike 30 also becomes pressurized. Sealing ring 52 is configured to hold that pressure, for example, up to eight psig.

Tip protector 50 also includes or defines one or more stabilizing rib 58a and 58b. Without stabilizing ribs 58a and 58b, tip protector 50 will vibrate about sealing ring 52 when cassette 10 and associated disposable components shipped along with the cassette are transported or moved. Such vibration can cause cap or tip protector 50 to loosen or come free from connector 30.

Stabilizing ribs 58a and 58b contact outer wall 38 of connector 30 and prevent such vibration from occurring. Although two stabilizing ribs 58a and 58b are illustrated, it should be appreciated that only one stabilizing rib or more than two stabilizing ribs may be provided as desired. Also, stabilizing ribs 58a and/or 58b may be moved further towards the distal end of tip protector 50 and connector 30.

Stabilizing ribs 58a and 548b are not continuous about inner wall 54 of tip protector 50 and instead are provided in segments about the inner wall and outer wall 38 of connector 30. That is, one or more opening 60 is provided through, within, or otherwise separating the structure of stabilizing ribs 58a and 58b. Openings 60 may provide a total opening that can be as low the micron level around the circumference of inner wall 54 of tip protector 50. That is, the structure of stabilizing ribs 58a and 58b may virtually all the way around the entire inner circumference of tip protector 50.

The purpose of openings 60 is to allow sterilizing gas to be introduced up through the lumen 36 of spike connector 30, out around outer wall 38 and through lumen 56, through the openings 60, such that sterilizing gas impinges and sterilizes (or substantially sterilizes) a surface 52a of sealing ring 52. Such flow path is illustrated by the phantom line arrow shown in FIG. 3 starting as the centerline of connector 30 and cap 50.

At the same time or at a different time, sterilizing gas is flowed around outer wall 62 of tip protector 50 as shown by the other arrowed phantom line. This outside gas impinges and sterilizes (or substantially sterilizes) surface 52b of sealing ring 52. In this manner, virtually all of sealing ring 52 is sterilized (or substantially sterilized) via a sterilizing gas, such as EtO. It should be noted that in a similar manner, stabilizing ribs 58a and 58b also include line contacts to the spike connector 30 and thus have the same method of sterilization as ring 52 in which sterilizing gas contacts both sides of ribs 58a and 58b at the line contact, but may not actually impinge the line contacts.

It has been found that the line contact between sealing ring 52 and outer wall 38 (and thus ribs 58a and 58b and outer wall 38), which may not be not impacted by the sterilizing gas, does not pose any significant risk of contamination. It is contemplated to provide the sterilizing gas onto surfaces 52a and 52b, sequentially or at the same time, depending upon ease of flowing the gas. Cassette 10 and the associated bags and tubes of the entire disposable set are provided inside of a bag or container that holds the sterilizing gas supplied on the outside of cassette 10 and tip protector 50.

Figure 4:
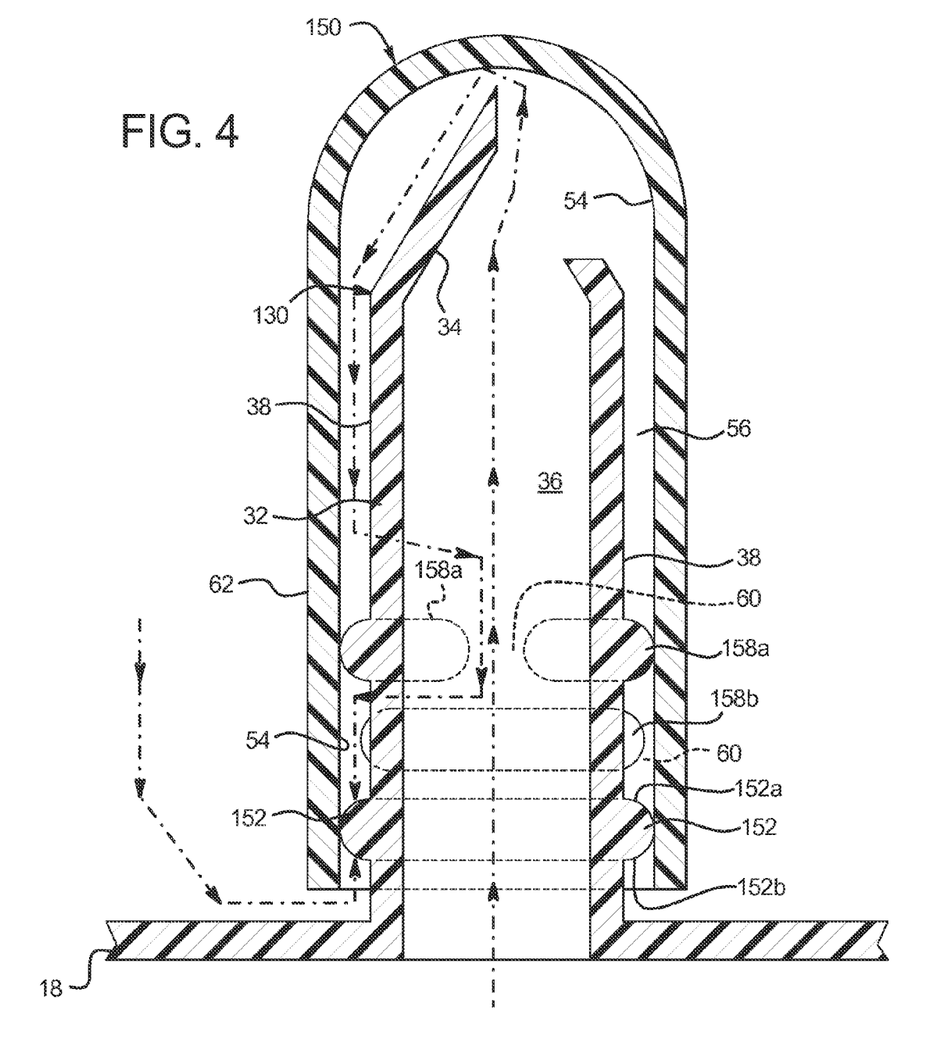
FIG. 4 is a side-sectional view illustrating another embodiment of a connector/cap configuration of the present disclosure.

Referring now to FIG. 4, an alternative connector 130 and alternative cap 150 are illustrated. Connector 130 and cap 150 are the same as connector 30 and cap 50, respectively, of FIG. 3 except that in FIG. 4, alternative sealing rings 152 and alternative stabilizing ribs 158a and 158b are provided on the outer surface 38 of connector 130. As seen by the phantom arrows, sterilizing gas, such as EtO flows in the same pathways as discussed above to contact surfaces 152a and 152b of alternative sealing ring 152.

Figures 5, 6:
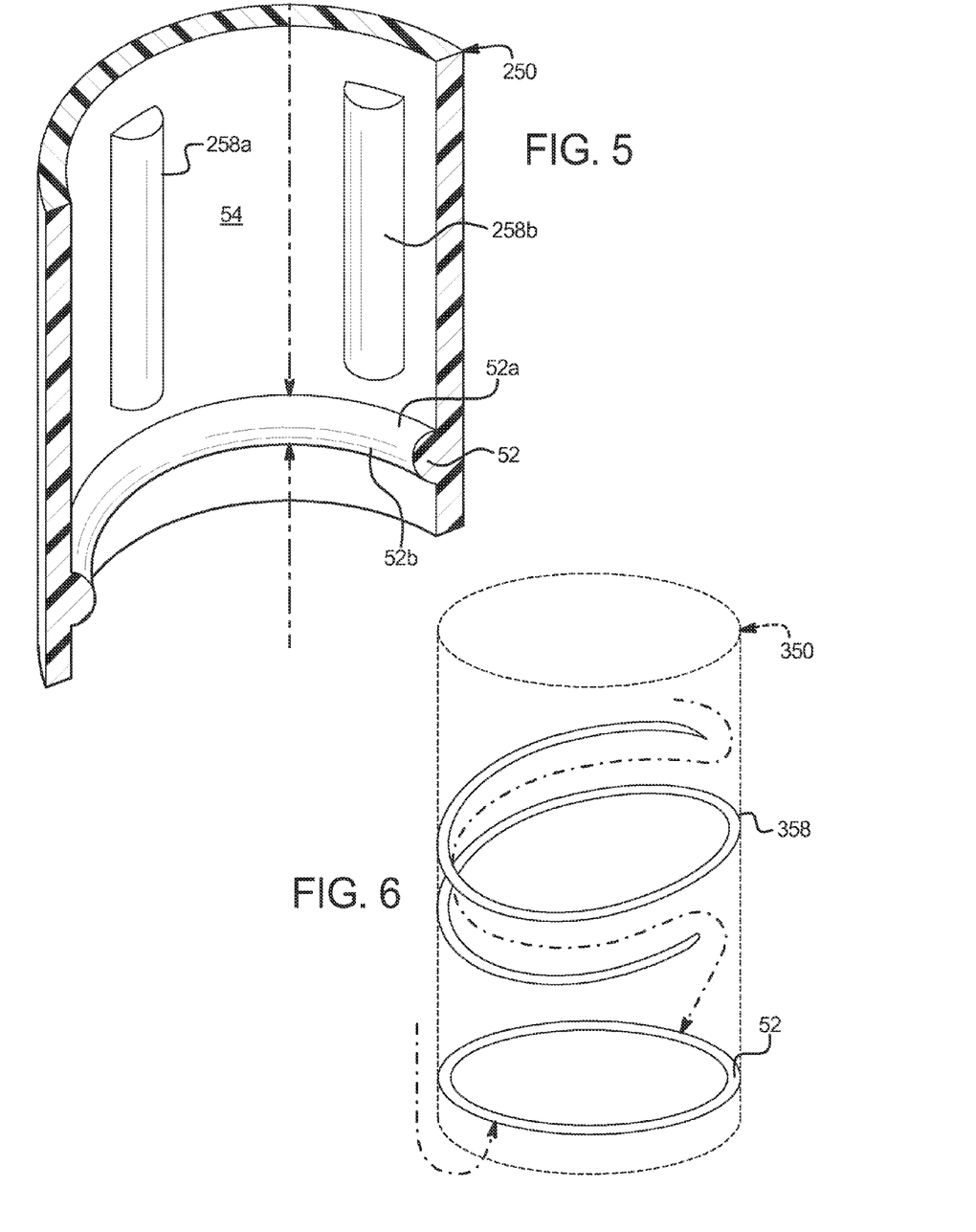
FIG. 5 is a sectional elevation view illustrating a further embodiment of a connector/cap configuration of the present disclosure.
FIG. 6 is a schematic elevation view illustrating yet another embodiment of a connector/cap configuration of the present disclosure.

Referring now to FIG. 5, a further alternative embodiment of the cap or tip protector is illustrated by cap 250. Cap 250 can operate for example with connector 30 shown in FIG. 3. Cap 250 includes the sealing ring 52 shown above in FIG. 3, which compresses against outer wall 38 of connector 30 to create a press-fit seal that holds a desired pressure. Sealing ring 52 includes surfaces 52a and 52b to be sterilized as described above.

Alternative vertical stabilizing ribs 258a and 258b extend inwardly from inner wall 54 of cap 250. The vertical ribs 258a and 258b allow sterilizing gas to proceed down along inner wall 54 through lumen 56, as seen by the phantom arrowed line, to impinge surface 52a of sealing ring 52 and sterilize (or at least substantially sterilize) surface 52a. Surface 52b is impinged via a sterilizing gas from beneath as shown via the upwardly directed arrowed line in FIG. 5. As before, ribs 258a and 258b are provided alternatively on outer wall 38 of connector 30.

Referring now to FIG. 6, a further alternative cap 350 is illustrated having a spiral or threadlike stabilizing rib 358. Here, as seen via the arrowed phantom line, sterilizing gas, such as EtO, spirals or winds its way around the corkscrew or threadlike spiral rib 358 until it reaches the end of the spiral rib and impinges sealing ring 52. Sealing ring 52 is also contacted via the sterilizing gas beneath as has been described herein.

Suitable materials for cassette 10 include a cyclic olefin copolymer ("COC") or a blend of COC with another olefin or acrylic, or other medically suitable relatively rigid plastic that can be sterilized via gas. Suitable materials for connectors 30 and 130 include any of the materials discussed above for cassette 10. Suitable materials for caps 50, 150, 250 and 350 include low density polyetylene ("LDPE") or a relatively softer or low density, olefin that may be semipermeable to EtO. Each of the structures discussed herein can be blow molded or injection molded.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A disposable dialysis apparatus comprising:
   a connector;
   a protective cap fitted to the connector;
   a sealing ring provided by one of the protective cap or the connector, the sealing ring forming a seal between the cap and the connector, the seal capable of holding pressure; and
   a stabilization rib provided by the connector, the stabilization rib (i) positioned and arranged to tend to prevent the protective cap from vibrating about the sealing ring, and (ii) discontinuous to define an opening enabling a sterilizing gas to flow past the stabilization rib to contact the sealing ring.

2. The disposable dialysis apparatus of claim 1, wherein the connector is at least one of: (i) a spike connector; (ii) a port connector extending from a disposable pumping cassette; or (iii) fitted to an end of a tube.

3. The disposable dialysis apparatus of claim 1, wherein the sealing ring and the stabilization rib are provided on the connector.

4. The disposable dialysis apparatus of claim 1, wherein the protective cap is a tip protector.

5. The disposable dialysis apparatus of claim 1, wherein the stabilization rib is at least one of: spiraling, or aligned with a central axis of the connector.

6. The disposable dialysis apparatus of claim 1, wherein the sterilizing gas flows past the stabilization rib to contact a first side of the sealing ring, and wherein the sterilizing gas is caused to further contact a second side of the sealing ring from a different direction.

7. The disposable dialysis apparatus of claim 1, wherein the stabilization rib is a first stabilization rib, and which includes at least one second stabilization rib provided by either the connector or the cap.

8. The disposable dialysis apparatus of claim 7, wherein the first stabilization rib is positioned radially along an outer wall of the connector, while the second stabilization rib is positioned axially along the outer wall of the connector.

9. The disposable dialysis apparatus of claim 7, wherein the second stabilization rib is positioned radially along an inner wall of the protective cap, while the first stabilization rib is positioned axially along an outer wall of the connector.

10. The disposable dialysis apparatus of claim 7, wherein the first stabilization rib is positioned radially along an outer wall of the connector, while the second stabilization rib is positioned axially along an inner wall of the protective cap.

11. A disposable dialysis apparatus comprising:
    a connector;
    a protective cap fitted to the connector;
    a sealing ring provided by one of the cap or the connector, the sealing ring forming a seal between the cap and the connector, the seal capable of holding pressure; and
    a stabilization rib provided by the protective cap, the stabilization rib (i) positioned and arranged to tend to prevent the protective cap from vibrating about the sealing ring, and (ii) discontinuous to define an opening enabling a sterilizing gas to flow past the stabilization rib to contact the sealing ring.

12. The disposable dialysis apparatus of claim 11, wherein the sealing ring and the stabilization rib are provided on the protective cap.

13. The disposable dialysis apparatus of claim 11, wherein the sterilizing gas flows past the stabilization rib to contact a first side of the sealing ring, and wherein the sterilizing gas is caused to further contact a second side of the sealing ring from a different direction.

14. The disposable dialysis apparatus of claim 11, wherein the stabilization rib is a first stabilization rib, and which includes at least one second stabilization rib provided by the protective cap,
    wherein one of the first or second stabilization ribs is positioned radially along an inner wall of the protective cap, while the other of the first or second stabilization ribs is positioned axially along the inner wall of the protective cap.

15. A disposable dialysis apparatus comprising:
    a cassette including at least one of a pump chamber and a valve chamber;
    a port connector extending from the cassette;
    a protective cap fitted onto the port connector;
    a sealing ring provided by one of the port connector or the protective cap, the sealing ring forming a seal between the port connector and the protective cap, the seal capable of holding a pressure; and
    a stabilization rib provided by one of the port connector or the protective cap, the stabilization rib (i) positioned and arranged to tend to prevent the cap from vibrating about the sealing ring, and (ii) segmented to enable a sterilizing gas to flow past the stabilization rib to contact the sealing ring.

16. The disposable dialysis apparatus of claim 15, wherein the cassette is in fluid communication with at least one of: (i) a heater bag or (ii) a drain bag.

17. The disposable dialysis apparatus of claim 15, wherein the port connector is a first port connector and the protective cap is a first protective cap, and wherein the cassette includes a second port connector and a second protective cap fitted onto the second port connector, at least one of the second port connector or the second protective cap providing a second stabilization rib.

18. The disposable dialysis apparatus of claim 15, wherein the sterilizing gas flows past the stabilization rib to contact a first side of the sealing ring, and wherein the sterilizing gas is caused to further contact a second side of the sealing ring from a different direction.

19. The disposable dialysis apparatus of claim 15, wherein the segmented stabilization rib defines openings that enable the sterilizing gas to flow past the stabilization rib to contact the sealing ring.

20. A disposable dialysis apparatus comprising:
    a connector;
    a protective cap fitted to the connector;
    a sealing ring provided by one of the protective cap or the connector, the sealing ring forming a seal between the cap and the connector, the seal capable of holding pressure; and
    a stabilization rib provided by one of the connector or the protective cap, the stabilization rib spiraling about the connector so as to (i) tend to prevent the protective cap from vibrating about the sealing ring, and (ii) spiral a sterilizing gas to flow past the stabilization rib to contact the sealing ring,
    wherein the stabilization rib is segmented.

21. The disposable dialysis apparatus of claim 20, wherein the spiraled sterilizing gas contacts a first side of the sealing ring, and wherein the sterilizing gas is caused to further contact a second side of the sealing ring from a different direction than the spiraled sterilizing gas.

* * * * *